United States Patent [19]

Dufresne et al.

[11] Patent Number: 5,310,949
[45] Date of Patent: May 10, 1994

[54] CHOLESTEROL LOWERING COMPOUNDS

[75] Inventors: Claude Dufresne, East Brunswick; Prakash S. Masurekar, Warren; Leslie A. Ferrell, Cranford; Deborah L. Zink, Manalapan; Margaret S. Sosa, Elizabeth, all of N.J.

[73] Assignee: Merck & Co., Inc., Rahway, N.J.

[21] Appl. No.: 939,258

[22] Filed: Sep. 2, 1992

[51] Int. Cl.$^5$ .................................. C07D 319/04
[52] U.S. Cl. .................................. 549/363
[58] Field of Search .................. 549/363; 514/452

[56] References Cited

U.S. PATENT DOCUMENTS

| | | | |
|---|---|---|---|
| 5,026,554 | 6/1991 | Bartizal | 549/363 |
| 5,096,963 | 3/1992 | Blain | 524/765 |
| 5,102,907 | 4/1992 | Bergstrom et al. | 549/363 |
| 5,132,320 | 7/1992 | Bergstrom et al. | 514/452 |

FOREIGN PATENT DOCUMENTS

WO92/12156  7/1992  European Pat. Off. .
0494622A1  7/1992  European Pat. Off. .

OTHER PUBLICATIONS

Baxter et al., Squalestatin 1, A Potent Inhibitor of Squalene Synthase Which Lowers Serum Cholesterol in Vivo, J. Biol. Chem., vol. 267 pp. 11705–11708 (1992).

Dawson, M. J. et al., . . . "The Squalestatins, Novel Inhibitors of Squalene Synthase . . . ", The Journal of Antibiotics, vol. 45, No. 5, pp. 639–647 (1992).

Sidebottom, P. J. et al., . . . "The Squalestatins, Novel Inhibitors of Squalene Synthase . . . ", The Journal of Antibiotics, vol. 45, No. 5, pp. 648–658 (1992).

*Primary Examiner*—Nicky Chan
*Attorney, Agent, or Firm*—Roy D. Meredith; Jack L. Tribble

[57] ABSTRACT

New Zaragozic acids have been isolated from a culture of MF5465. These compounds and their derivatives are active as squalene synthetase inhibitors and are useful in the treatment of hypercholesterolemia.

9 Claims, No Drawings

CHOLESTEROL LOWERING COMPOUNDS

BACKGROUND OF THE INVENTION

This case is related to Merck case 18662.

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR® (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analog containing compounds such as those described in P. Ortiz de Montellano et al, J. Med Chem. 20, 243 (1977) and E. J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthetase.

Recently certain nonphosphorous containing inhibitors of squalene synthetase have been isolated as natural products. These natural product inhibitors are described in U.S. Pat. Nos. 5,053,425; 5,055,487 and 5,026,554. Certain squalestatins are discussed in Baxter, A. et al., J. Biol. Chem. 267, 11705 (1992); Dawson, M. J. et al., J. Antib. 45, 639 (1992); Sidebottom, P. J. et al., Antib. 45,648 (1992). See also EPO 494622 and PCT WO 92/12156.

U.S. Pat. No. 5,026,554 describes a squalene synthetase inhibitor of structure:

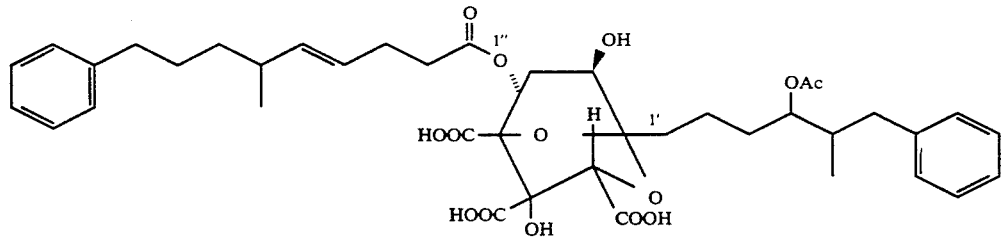

which is hereafter referred to as Zaragozic acid C. This compound is produced by a solid fermentation employing a culture of *Leptodontium elatius*. The present invention discloses certain structurally related compounds to Zaragozic acid C which have now been isolated as minors from a fermentation broth using *Leptodontium elatius*.

DETAILED DESCRIPTION OF THE INVENTION

The compounds of the structural formula (I), or their pharmaceutically acceptable salts, are useful in the treatment of hypercholesterolemia, fungal infections, and cancer. Structural formula (I) consists of

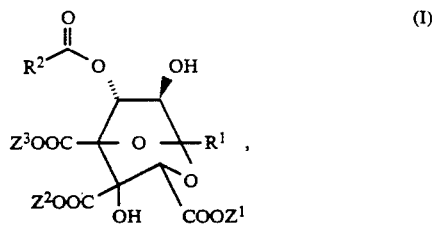

or pharmaceutically acceptable salt thereof, wherein $R^1$ is selected from the group consisting of

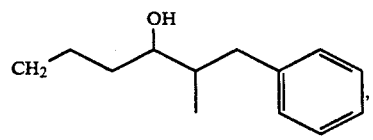

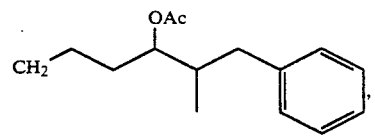

or

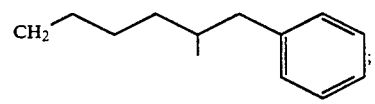

$R^2$ is selected from the group consisting of

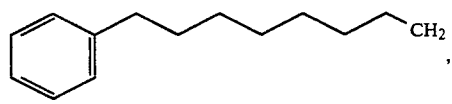

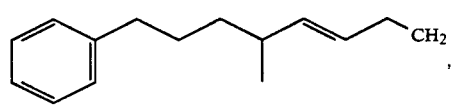

or

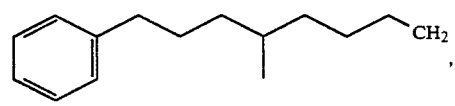

3

-continued

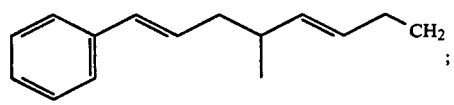

$Z^1$, $Z^2$ and $Z^3$ are each independently selected from;
a) H;
b) $C_{1-5}$alkyl;
c) $C_{1-5}$alkyl substituted with a member of the group consisting of:
  i) phenyl,
  ii) phenyl substituted with methyl, methoxy, halogen (Cl, Br, I, F) or hydroxy;
with the proviso that when $R^2$ is

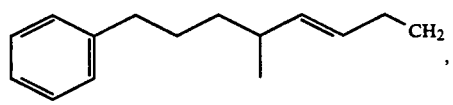

4 then $R^1$ is neither

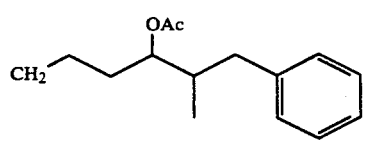

nor,

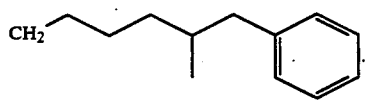

One embodiment of the present invention is formula I compounds further restricted to compounds wherein $Z^1$, $Z^2$ and $Z^3$ are each independently H or $CH_3$.

Another embodiment is a compound selected from the group consisting of the following structures,

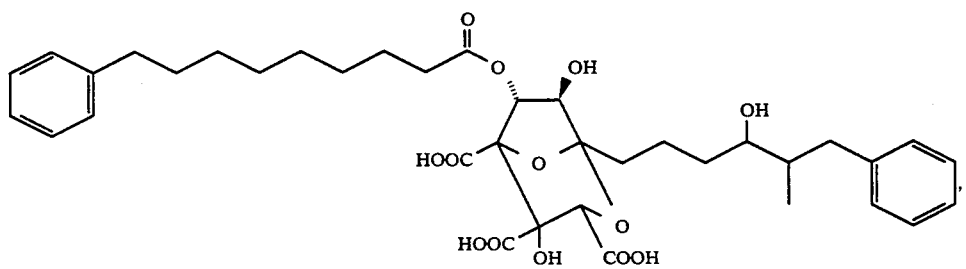

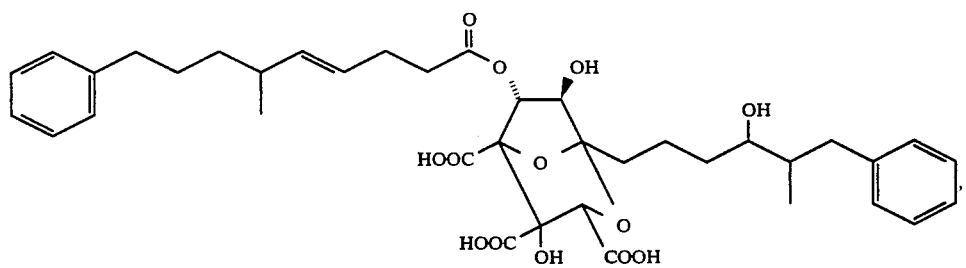

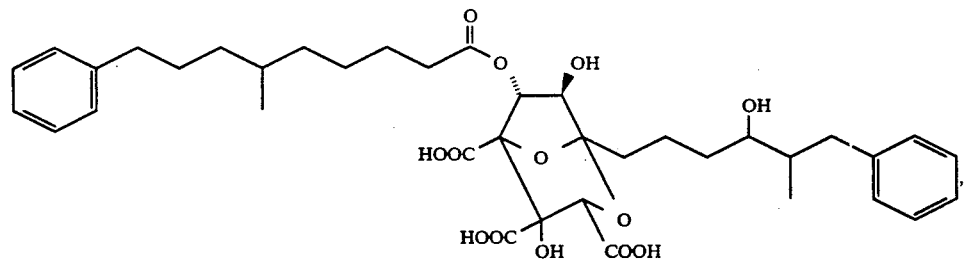

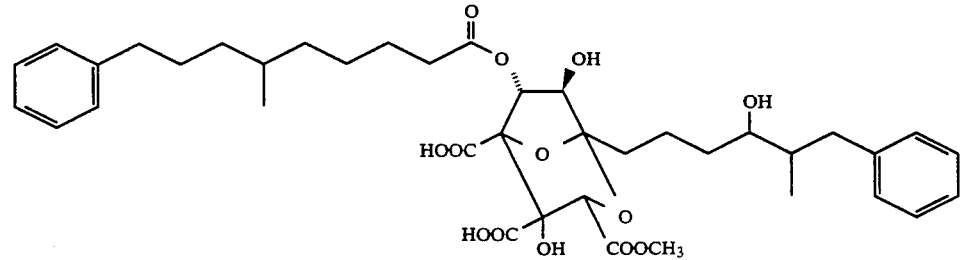

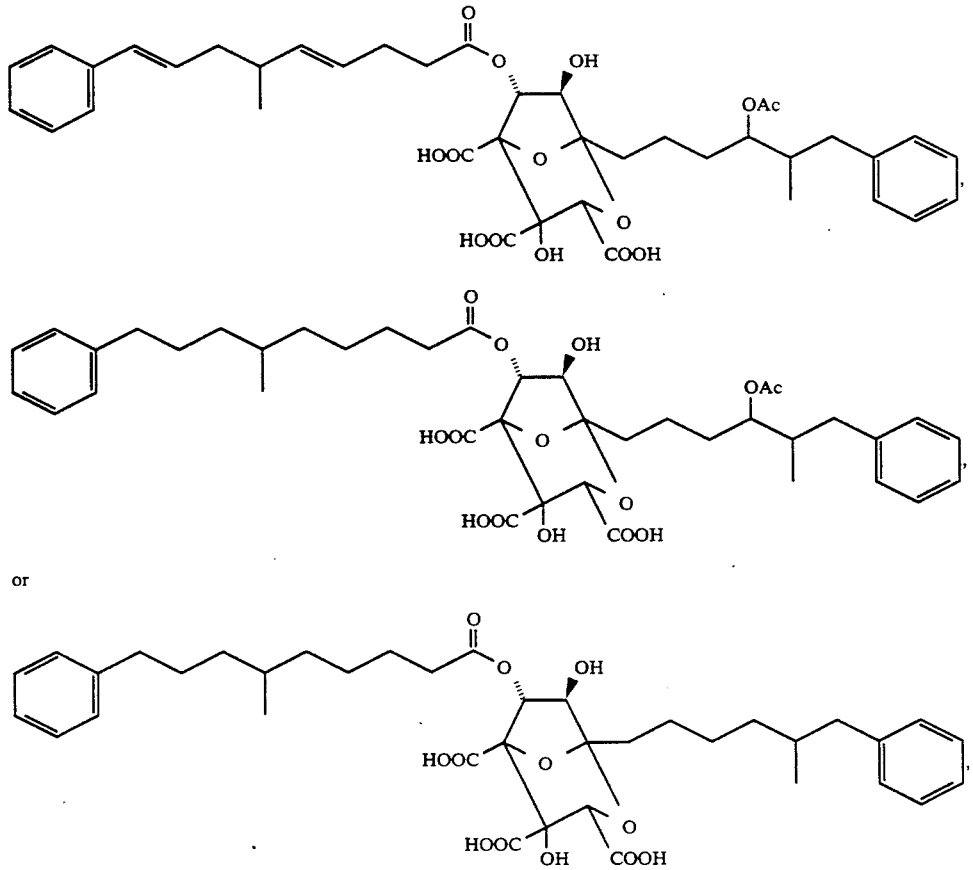

or

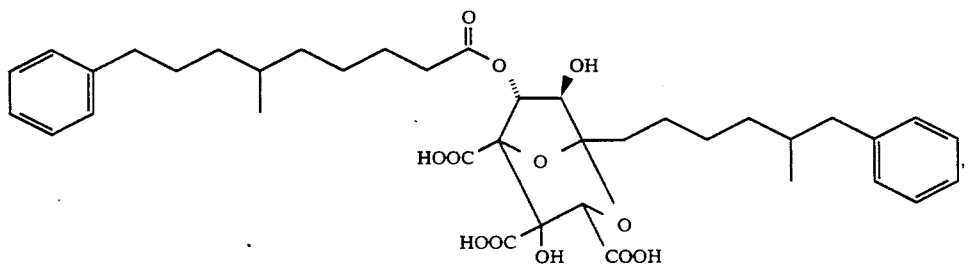

or a pharmaceutically acceptable salt thereof.

The present invention is directed to certain zaragozic acid derivatives isolated from the fermentation of MF 5465.

The compounds of formula (I) can be prepared in an aerobic fermentation procedure employing a fungal culture, MF5465, identified as *Leptodontium elatius*. This fermentation procedure is described in U.S. Pat. No. 5,026,554, the contents of which are herein specifically incorporated by reference.

The compounds of the present invention have been isolated as components produced in lower yield then Zaragozic acid C from this fermentation procedure.

Mutants of MF5465, having essentially the same characteristics as MF 5465, are also capable of producing compounds of this invention.

The culture MF5465 is that of a fungus, a lignicolous Hyphomycete, *Leptodontium elatius*, isolated from wood in the Joyce Kilmer Memorial Forest in North Carolina. This culture has been deposited with the American Type Culture Collection at 12301 Parklawn Drive, Rockville, Md. 20852 as ATCC 74011.

The characteristics of MF5465 are described in U.S. Pat. No. 5,026,554.

Compounds of this invention can be obtained by culturing the above noted microorganism in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glycerin, glucose, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen include complex sources such as peptone, yeast extracts (hydrolysates, autolysates), dried yeast, tomato paste, soybean meal, corn steep liquor, distillers solubles, malt extracts and the like. Inorganic nitrogen sources such as ammonium salts (e.g., ammonium nitrate, ammonium sulfate, ammonium phosphate, etc.) or other nitrates or nitrites can also be used. The various sources of nitrogen can be used alone or in combination in amounts ranging between 0.2 to 70 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polypropylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure begins by inoculating a preserved source of culture (spores or mycelia) into a nutrient seed medium and obtaining, sometimes through a multi step process, growth of the organism which serves as inoculum for the production of the active compounds. After inoculation, the flasks are incubated with rotary shaking at temperatures ranging from 20° to 30° C., preferably 25° to 28° C. Shaking rates may range up to 400 rpm, preferably 200 to 220 rpm. Seed flasks are incubated over a period of 2 to 10 days, preferably 2 to 4 days. When biomass is plentiful, usually 2 to 4 days, the culture may be used to inoculate production medium flasks. Additional seed stages are required when using larger vessels for production. When this is done, a portion of the culture is used to inoculate a subsequent seed flask or fermentor which is incubated under similar conditions.

After inoculation, the production fermentation is incubated for 3 to 30 days, preferably 7 to 21 days, with or without agitation (depending on whether liquid or solid fermentation media are employed). The fermentation is conducted aerobically at temperatures ranging from 20° to 40° C. If used, agitation or shaking may be at a rate of 100 to 400 rpm. To obtain optimum results, the temperatures are in the range of 22° to 28° C., most preferably 24° to 26° C. The pH of the nutrient medium suitable for producing the active compounds is in the range of 3.5 to 8.5, most preferably 5.0 to 7.5. After the appropriate period for production of the desired compound, fermentation flasks or fermentors are harvested and the active compound isolated.

An organic solvent is employed to extract a compound of this invention from the fermentation medium. The preferred solvent for extraction of the fermentation broth is a water immiscible solvent such as isopropyl acetate. The mixture of organic solvent and fermentation broth is vigorously stirred and filtered. The organic extract is then adsorbed on an anion exchange resin. The preferred resin is a weekly basic anion exchange resin such as AMBERLYST A-21 (acetate cycle). The active compounds can be eluted from AMBERLYST A-21 using a low pH solution or a high salt eluant. The preferred eluant is 3% ammonium chloride in 90% methanol/water. After elution from the ion exchange resin, the active compounds may be recovered from the eluate by diluting the eluate with water, acidifying to pH<3, and extracting into an organic solvent. The preferred solvent for extraction is ethyl acetate. The organic extract is then evaporated to afford a partially purified complex of active compounds.

The complex of active compounds is further purified by chromatographic separation which may be carried out by employing reverse phase chromatography. The HPLC column packing, also known as adsorbent, may include octyl, octadecyl, phenyl, cyano, or diol bonded silica gel, alumina, or polymer. The preferred adsorbent for this chromatography is a C8 bonded phase silica gel. The mobile phase of the eluant comprises methanol, actonitrile, or tetrahydrofuran as an organic modifier for an aqueous solution buffered at a pH in the range of 2 to 8. The preferred eluant for reverse phase chromatography is a mixture of acetonitrile and water buffered at a low pH, such as 0.1% phosphoric acid, or trifluoroacetic acid. The flow rate ranges from 0.5 to 4 ml/min for a column of approximately 5 mm ID. The temperature of the column ranges between 10° C. and 45° C.

The relative retention time (RRT) is the ratio of the retention time of a given major peak under given chromatographic conditions, divided by the retention time of Zaragozic acid C under identical chromatographic conditions. The structure of Zaragozic acid C is provided in the Background of the Invention, above.

The present invention is also directed to a method of treating hypercholesterolemia which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The present invention is also directed to a method of inhibiting squalene synthetase which comprises the administration to a subject in need of such treatment a nontoxic therapeutically effective amount of a compound represented by structural formula (I) and pharmaceutically acceptable salts thereof. Specifically, the compounds of this invention are useful in treating disease conditions such as, but not limited to, hypercholesterolemia which result from the action of the enzyme squalene synthetase. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form.

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-COA synthase inhibitors, and squalene expoxidase inhibitors. Illustrative of such inhibitors are lovastatin, simvastatin, pravastatin and fluvastatin. Other cholesterol lowering agents that may be administered include niacin, probucol, and the fibric acids, clofibrate and gemfibrozil. Appropriate daily dosages for adults are niacin (2-8 gm), probucol (up to 1000 mg), clofibrate (up to 2 gm) and gemfibrozil (800-1500 mg).

The compounds of this invention may also be coadministered with pharmaceutically acceptable nontoxic cationic polymers capable of binding bile acids in a non-reabsorbable form in the gastro-intestinal tract. Examples of such polymers include cholestyramine, colestipol and poly[methyl-(3-trimethylaminopropyl-)imino-trimethylene dihalide]. The relative amounts of the compounds of this invention and these polymers is between 1:100 and 1:15,000.

The intrinsic squalene synthetase inhibitory activity of representative compounds of this invention is measured by the standard in vitro protocol described below:

Preparation of Microsomes

Male, Charles River CD rats (120 to 150 g) are fed a diet containing 0.1% lovastatin for 4 days. The livers from these rats were homogenized in 5 volumes (ml/g) of ice cold 50 mM HEPES (4-(2-hydroxyethyl)-1-piperazine-ethanesulfonic acid), 5 mM EDTA(ethylenediaminetetraacetic acid) pH 7.5 with a Potter-Elvehjem type tissue grinder. The homogenate is centrifuged twice at 20,000×g for 15 minutes at 4° C., discarding the pellet each time. The supernatant is then centrifuged at 100,000×g for 1 hour at 4° C. The resulting microsomal pellet is resuspended in a volume of the above homogenizing buffer equal to one-fifth the volume of the original homogenate. This microsomal preparation typically has a protein concentration of about 7 mg/ml. The microsomal suspensions are stored in aliquots at −70° C. Squalene synthetase activity in these aliquots is stable for at least several months.

Partial Purification of Prenyl Transferase

Prenyl transferase is purified to use in the enzymatic synthesis of radiolabelled farnesyl pyrophosphate. Prenyl transferase is assayed by the method of Rilling (Methods in Enzymology 110, 125-129 (1985)) and a unit of activity is defined as the amount of enzyme that will produce 1 μmole of farnesyl pyrophosphate per minute at 30° C. in the standard assay.

The livers of 23 forty-day old male rats that have been fed 5% cholestyramine plus 0.1% lovastatin are homogenized in a Waring blender in 1 liter of 10 mM mercaptoethanol, 2 mM EDTA, 25 μM leupeptin, 0.005% phenylmethyl sulfonyl fluoride pH 7.0 containing 0.1 trypsin inhibitor units of aprotinin/ml. The homogenate is centrifuged at 20,000×g for 20 minutes. The supernatant is adjusted to pH 5.5. with 6N HOAc and centrifuged at 100,000×g for 1 hour. This supernatant is adjusted to pH 7.0 with 3N KOH and a 35–60% ammonium sulfate fraction taken. The 60% pellet is redissolved in 60 ml of 10 mM potassium phosphate, 10 mM mercaptoethanol, 1 mM EDTA pH 7.0 (Buffer A) and dialyzed against two 1 liter changes of Buffer A. This dialyzed fraction is applied to a 12.5×5 cm column of DEAE-sepharose 4B equilibrated with Buffer A. The column is washed with 700 ml of Buffer A and a 1 liter gradient from Buffer A to 100 mM potassium phosphate, 10 mM mercaptoethanol, 1 mM EDTA pH 7.0. Fractions having a specific activity greater than 0.20 units/mg are combined, solid ammonium sulfate is added to bring to 60% saturation and pelleted. The pellet is dissolved in 8 ml of 10 mM Tris, 10 mM β-mercaptoethanol pH 7.0 (Buffer B). The redissolved pellet is taken to 60% saturation with ammonium sulfate by adding 1.5 volumes of saturated ammonium sulfate in Buffer B. This ammonium sulfate suspension typically contains 3.5 units/ml with a specific activity of 0.23 units/mg and is free of isopentenyl pyrophosphate isomerase activity. This ammonium sulfate suspension is used for the synthesis of [4-$^{14}$C]farnesyl-pyrophosphate and its activity is stable stored at 4° C. for at least 6 months.

Enzymatic Synthesis of [4-$^{14}$C]farnesyl-pyrophosphate

The solvent (ethanol: 0.15N NH$_4$OH, 1:1) is removed from 55 μCi of [4-$^{14}$C]isopentenyl pyrophosphate (47.9 μCi/μmole) by rotary evaporation. Six hundred microliters of 100 mM Tris, 10 mM MgCl$_2$, 4 mM dithiothreitol pH 7.5 is added and the solution is transferred to a 1.5 ml Eppendorf centrifuge tube. Geranyl-pyrophosphate, 250 μl of a 20 mM solution, and 50 μl of the ammonium sulfate suspension of prenyl transferase are added to initiate the reaction. This incubation contains 5 μmoles of geranyl pyrophosphate, 1.15 μmoles of isopentenyl pyrophosphate, 6 μmoles of MgCl$_2$ of 0.18 units of prenyl transferase in a volume of 900 μl. The incubation is conducted at 37° C. During the incubation, the mix typically turns cloudy white as the newly formed magnesium complex of farnesyl pyrophosphate precipitates out of solution. The [4-$^{14}$C]farnesyl pyrophosphate is collected by centrifugation for 3 minutes at 14,000 rpm in an centrifuge tube, the supernatant removed, and the pellet is dissolved in 1.0 ml of 50 mM HEPES, 5 mM EDTA, pH 7.5. The yield is typically about 50 μCi (90%) of [4-$^{14}$C]farnesyl pyrophosphate. The [4-$^{14}$C]farnesyl pyrophosphate is stored in aliquots at −70° C.

Squalene Synthetase Assay

Reactions are preformed in 16×125 mm screw cap test tubes. A batch assay mix is prepared from the following solution:

|   |   | ml per assay | volume for 50 assays |
|---|---|---|---|
| 1. | 250 mM Hepes pH 7.5 | 20 | 1000 |
| 2. | NaF 110 mM | 10 | 500 |
| 3. | MgCl$_2$ 55 mM | 10 | 500 |
| 4. | Dithiothreitol 30 mM | 10 | 500 |
| 5. | NADPH 10 mM (made fresh) | 10 | 500 |
| 6. | [4-$^{14}$C]farnesyl-pyrophosphate 47.9 μCi/μmole, and 0.025 μCi/3.0 μl | 3.0 | 150 |
| 7. | H$_2$O | 24 | 1200 |

This assay mix is degassed under a vacuum and flushed with N$_2$. Solutions of the squalene synthetase inhibitors are prepared either in DMSO or MeOH and a 1:120 dilution of the microsomal protein is made with the original homogenizing buffer. For each reaction, 87 μl of the assay mix is taken with 3 μl of an inhibitor solution (DMSO or MeOH in the controls), warmed to 30° C. in a water bath and then the reaction is initiated by the addition of 10 μl of the 1:120 dilution of microsomal protein (0.6 μg protein total in the assay). The reactions are stopped after 20 minutes by the addition of 100 μl of a 1:1 mix of 40% KOH with 95% EtOH. The stopped mix is heated at 65° C. for 30 minutes, cooled, 10 ml of heptane is added and the mix is vortexed. Two grams of activated alumina is then added, the mix vortexed again, the alumina allowed to settle and 5 ml of the heptane layer is removed. Ten ml of scintillation fluid is added to the heptane solution and radioactivity is determined by liquid scintillation counting.

Percent inhibition is calculated by the formula:

$$1 - \frac{[\text{Sample} - \text{Blank}]}{[\text{Control} - \text{Blank}]} \times 100$$

$IC_{50}$ values are determined by plotting the log of the concentration of the test compound versus the percentage inhibition. The $IC_{50}$ is the concentration of inhibitor that gives 50% inhibition as determined from these plots.

The present compounds are also useful as broad spectrum antifungal agents as determined by broth and agar dilution methods. Thus the present invention is also directed to a method of treating fungus infections which comprises the administration to an organism in need of such treatment a nontoxic therapeutically effective amount of a compound represented by the structural formula (I) and pharmaceutically acceptable salts thereof. Generally from 2 to about 20 mg/kg should be employed as a unit dosage in an antifungal treatment.

Furthermore the compounds of the present invention are useful as inhibitors of farnesyl-protein transferase and thereby of farnesylation of the RAS protein and thus block the ability of RAS to transform normal cells to cancer cells. Farnesyl-protein transferase activity may be reduced or completely inhibited by adjusting the compound dose.

The intrinsic farnesyl-protein transferase (FTase) activity of representative compounds of this invention is measured by the assays described below:

RASIT ASSAY I

Farnesyl-protein transferase (Ftase) from bovine brain is chromatographed on DEAE-Sephacel (Pharmacia, 0–0.8M NaCl gradient elution), N-octyl agarose (Sigma, 0–0.6M Nacl gradient elution), and a mono Q HPLC column (Pharmacia, 0–0.3M NaCl gradient). Ras-CVLS at 3.5 $\mu$M, 0.25 $\mu$M [$^3$H]FPP, and the compounds to be assayed are incubated with this partially purified enzyme preparation.

RASIT ASSAY II

Farnesyl-protein transferase (Ftase) from bovine brain is chromatographed on DEAE-Sephacel (Pharmacia, 0–0.8M NaCl gradient elution), N-octyl agarose (Sigma, 0–0.6M Nacl gradient elution), and a mono Q HPLC column (Pharmacia, 0–0.3M NaCl gradient). Ras-CVLS at 1.0 $\mu$M, 0.5 $\mu$M [$^3$H]FPP, and the compounds to be assayed are incubated with this partially purified enzyme preparation. The Ftase data is a measurement of the ability of the test compound to inhibit Ras farnesylation in vitro.

The pharmaceutical compositions containing the compounds of structural formula I inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal a day.

The following Examples illustrate the preparation of the compounds of formula (I) and their incorporation into pharmaceutical compositions and, as such, are not to be considered as limiting the invention set forth in the claims appended hereto.

EXAMPLE 1

Fermentation of *Leptodontium elatius* at the 500 L Scale

Seed Stock Preparation

*Leptodontium elatius* (MF5465) was obtained from the MSDRL culture collection as a lyophilized preparation (order #, N920316001). The working seed stock was prepared by inoculating a 250 ml flask containing 50 ml of seed medium with the lyophilized culture and incubating for 48 hours at 25° C. with 220 RPM rotary shaking. The seed medium contained per liter in deionized water: soluble starch, 30 gm; cerelose, 10 gm; pharmamedia, 10 gm; $KH_2PO_4$, 9 gm; DIFCO yeast extract (8005), 5 gm; $MgSO_4 \cdot 7H_2O$, 0.2 gm; $FeSO_4 \cdot 7H_2O$, 10 mg; $MnSO_4 \cdot H_2O$, 10 mg; $CuCl_2 \cdot 2H_2O$, 0.25 mg; $CaCl_2 \cdot 2H_2O$, 0.75; $H_3BO_4$, 0.56 mg; $ZnSO_4 \cdot 7H_2O$, 2.0 mg; $(NH_4)_6Mo_7O_{24} \cdot 4H_2O$, 0.19 mg, and the pH was adjusted to 6.0 with sodium hydroxide. After the 48 hour incubation period, 2 ml of the culture were transferred to each of a second set of 4 four flasks containing seed medium as described above. Incubation conditions were identical to those described above. After incubation of the 4 second generation cultures, the 200 ml of culture broth contained in the 4 flasks was combined with 100 ml of 30% glycerol and the resultant mixture was aliquoted at 1 ml/cryovial and stored at −70° C. These aliquots of frozen vegetative mycelia (FVM) were used to initiate inoculum development.

Inoculum Development

One FVM was used to inoculate each 250 ml flask containing 50 ml of seed medium. The cultures were incubated at 25° C. with 220 RPM rotary shaking for 48 hours. Twenty milliliters were transferred to each 2 L flask containing 500 ml of seed medium. The cultures were incubated at 25° C. with 220 RPM rotary shaking for 48 hours. Four 2 L scale cultures were combined (2 L total culture volume) and used to inoculate a 285 L fermentor containing 180 L of seed medium (with 2 ml/L polypropylene glycol to suppress foaming). The fermentation was carried out for 48 hours under the following conditions: temperature, 25° C.; pressure, 0.7 Kg/cm$^2$; air flow, 75 liters/min.; agitation, 200 RPM.

Production Fermentation

Twenty-five liters from the seed fermentation were inoculated into a 760 liter fermentor containing 500 L of production medium which contained per liter in deionized water: primatone HS, 23 gm; DIFCO yeast extract (8005), 7.5 gm; sodium citrate, 11 gm; glycerol (sterilized separately as a 50% w/v solution), 20 gm; polypropylene glycol, 0.5 ml, and the pH was adjusted to 6.0 with sulfuric acid. The medium was sterilized for 30 minutes at 123° C. and the fermentation was carried out for approximately 19 days under the following conditions: temperature, 25° C.; pressure, 0.7 Kg/cm$^2$; air flow, 100 liters/min.; agitation, 160 RPM. pH was allowed to rise from approximately 6.0 (post-inoculation) and was controlled at 7.2 with sulfuric acid. Residual glycerol was monitored and as the concentration approached 5 gm/L, glycerol was added to the fermentor as a sterile 50% w/v solution to give a final concentration of approximately 20 gm/L.

EXAMPLE 2

Isolation Process:

The whole broth (1500 L, which is three combined batches prepared by Example 1) was acidified to pH 2.3 with sulfuric acid. The broth was extracted twice with isopropyl acetate (1500 L each time). (For each extraction, isopropyl acetate was added and the mixture was agitated for 1 hour. The isopropyl acetate extract was recovered from the mixture using a Westfalia Decanter.) The two extracts were combined (3000 L) and applied to an AMBERLYST A-21 (OAc cycle) column (132 L bed volume). The resin was prepared by stirring it in 1N acetic acid before packing into the column. The resin bed was successively washed with MeOH (132 L) and isopropyl acetate (132 L). After the isopropyl acetate extract was passed through the column, the column was washed with 50% MeOH/H$_2$O (132 L). The spent and wash were discarded. The column was then eluted with 3% NH$_4$Cl in 90% MeOH/H$_2$O (1320 L). The eluate (1320 L) was diluted with water (402 L) and loaded onto an HP-20 column (95 L). The spent and wash were discarded. The column was eluted with 90% MeOH/H$_2$O (380 L). The HP-20 eluate was diluted with water (380 L) and adjusted to pH 2.3 with concentrated sulfuric acid. EtOAc (570 L) and water (380 L) were then added. The EtOAc layer (492 L) was separated and concentrated under reduced pressure to an oily residue.

The residue was dissolved in acetonitrile (500 mL) and this solution was diluted with 65% acetonitrile/35% 0.1% phosphoric acid in water (250 ml). A 75 mL aliquot was injected onto a preparative HPLC column. The column consisted of an Amicon Matrex LC ODS Silica (10 cm ID×50 cm) with 100 Å 20 μm particle size. Elution was carried out with a mobile phase of 65% CH$_3$CN/35% 0.1% H$_3$PO$_4$ in H$_2$O at a flow rate of 250 mL/min, collecting fractions at four minute intervals to provide 1 L fractions, and detecting at 220 mm. The fractions were pooled as follows: fractions #3–4; fractions #5–6; fraction #7; fractions #8–9; fractions #10–11; fractions #12–14; fractions #15–17 and fractions #18–20. A total of 10 injections were performed, combining pooled fractions from each run, to give Cut 3–4, Cut 5–6, Cut 7, Cut 8–9, Cut 10–11, Cut 12–14, Cut 15–17, Cut 18–20. Cuts 5–6, 8–9, 12–14, and 18–20 were further fractionated using preparative HPLC.

Cut 5–6

Cut 5–6 was partitioned with an equal volume of EtOAc. The organic layer was evaporated to dryness. One half of the dry residue from Cut 5–6 was dissolved in 3 mL of CH$_3$CN and 1 mL of 0.1% H$_3$PO$_4$ in H$_2$O was added. This solution was injected on a preparative HPLC column (Dynamax C8 8 μm 41.4 mm ID×250 mm L+guard) eluting with 60% CH$_3$CN/40% 0.1% H$_3$PO$_4$ in H$_2$O at a flow rate of 24 mL/min. Fractions were collected at 1 minute intervals (detecting wavelength=220 nm). Each of the following fractions was analyzed by analytical HPLC and then extracted with an equal volume of EtOAc. The organic layer was evaporated to dryness to afford dry material.

The analytical HPLC conditions involved a reverse-phase silica-based HPLC column (Dynamax C8, 60 Angstroms, 8 μm particles, 4.6 mm 1D×250 mm with guard column) eluting at room temperature at a flow rate of 1 ml/min with a mobile phase of 55% CH$_3$CN/45% of 0.1% H$_3$PO$_4$ in H$_2$O. The detection wavelength was 205 nm. Relative retention time to zaragozic acid C(RRT) is calculated for each compound as the ratio of the retention time of a given major peak divided by the retention time zaragozic acid C (30.5 min.).

Fraction 27 (6.6 mg) and 28 (5.1 mg): Each contain at least 2 components. The components have the molecular weights 710 and 770 by FAB-MS (observed [M-H]$^-$ at m/z 709 and 769, respectively). The 710 component has the molecular formula C$_{38}$H$_{46}$O$_{13}$ as determined by HR-EI measurement of the trimethyl ester derivatives (calc. for C$_{38}$H$_{46}$O$_{13}$+(CH$_2$)$_3$ —H$_2$O; 734.3302 found 734.3299).

Relative Retention Time (RRT)=0.30.

Fraction 30 (7 mg): contains a major component. The component has the molecular weight 728 by FAB-MS (observed [M-H]$^-$ at m/z 727. It has the molecular formula C$_{39}$H$_{52}$O$_{13}$, as determined by HR-EI measurement of the trimethyl ester derivatives (calc. for C$_{39}$H$_{52}$O$_{13}$+(CH$_2$)$_3$ —H$_2$O; 752.3772, found 752.3750).

Relative Retention Time (RRT)=0.37

Fraction 31 (21.1 mg): contains at least 2 major components. The components have the molecular weights 698 and 712 by FAB-MS (observed [M-H]$^-$ at m/z 697 and 711 respectively). They have the molecular formulas C$_{37}$H$_{46}$O$_{13}$ and C$_{38}$H$_{48}$O$_{13}$ as determined by HR-EI measurement of the trimethyl ester derivatives (calc. for C$_{37}$H$_{46}$O$_{13}$+(CH$_2$)$_3$ —H$_2$O; 722.3233, found 722.3268 and calc for C$_{38}$H$_{48}$O$_{13}$+(CH$_2$)$_3$ —CH$_3$COOH; 736.3459 found 736.3444).

Relative Retention Time (RRT)=0.38

Fraction 33 (8.1 mg): contains at least 2 components. The components have the molecular weight 710 and 768 by FAB-MS (observed [M-H]$^-$ at m/z 709 and 767 respectively). The 710 component has the molecular formula C$_{38}$H$_{46}$O$_{13}$ as determined by HR-EI measurement of the trimethyl ester derivative (calc. for C$_{38}$H$_{46}$O$_{13}$+(CH$_2$)$_3$ —H$_2$O; 734.3302, found 734.3291.

Relative Retention Time (RRT)=0.41.

Fraction 36 (10.1 mg): The major component in this fraction has a molecular weight of 700 by FAB-MS (observed [M-H]⁻ at m/z 699). The molecular formula $C_{37}H_{48}O_{13}$ was determined by HR-EI measurement of the trimethylester derivative [calc. for $(C_{37}H_{48}O_{13}+(CH_2)_3$ —$H_2O)$ 724.3459, found 724.3458]. The major component has a RRT=0.46 and may be 4'-O-desacetyl-4'',5'''-dihydro-6''-desmethyl-zaragozic acid C, MW 700, of the structure:

Angstroms, 8 μm particles, 4.6 mm ID×250 mm with guard column) eluting at room temperature at a flow rate of 1 ml/min with a mobile phase of 55% $CH_3CN/45\%$ of 0.1% $H_3PO_4$ in $H_2O$. The detection wavelength was 205 nm. Relative retention time to zaragozic acid C(RRT) is calculated for each compound as the ratio of the retention time of a given major

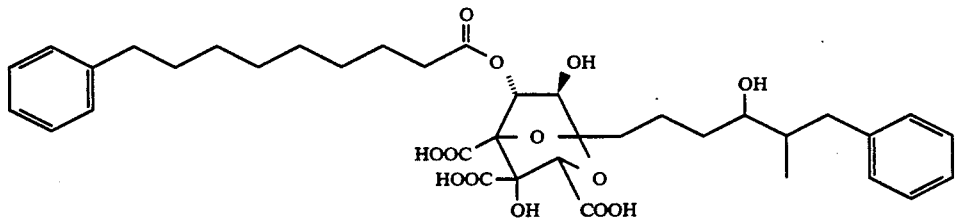

Fraction 38 (31.2 mg): The major component in this fraction has a molecular weight of 712 by FAB-MS (observed [M-H]⁻ at m/z 711). The molecular formula $C_{38}H_{48}O_{13}$ was determined by HR-EI measurement of the trimethylester derivative [calc. for $(C_{38}H_{48}O_{13}+(CH_2)_3$ —$H_2O)$ 736.3459, found 736.3451]. The major component has RRT=0.49 and may be 4'-O-desacetyl-zaragozic acid C MW 712.

Cut 7

Contains 4'-O-desacetyl-zaragozic acid C MW 712 (10.0 g), RRT=0.49 peak divided by the retention time of zaragozic acid C (30.5 min).

Fractions 31–32: contains 2 compounds MW 714, 738. The 714 component has a molecular weight of 714 by FAB-MS (observed [M-H]⁻ at m/z 713). Its molecular formula $C_{38}H_{50}O_{13}$ was determined by HR-EI measurement of the trimethylester derivative [calc. for $(C_{38}H_{50}O_{13}+(CH_2)_3$ —$H_2O)$ 738.3615, found 738.3606]. The 714 component has RRT=0.58 and may be 4'-O-desacetyl-4'',5''-dihydro-zaragozic acid C, of the structure:

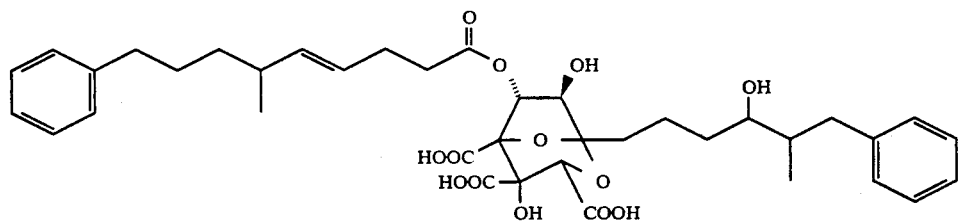

Cut 8–9

One tenth of Cut 8–9 was partitioned with an equal volume of EtOAc. The organic layer was evaporated to dryness. The dry residue was dissolved in 2 mL of $CH_3CN/0.5$ mL of 0.1% $H_3PO_4$ in $H_2O$. This solution was injected on a preparative HPLC column (Dynamax C8 8 μm 41.4 mm ID×250 mm L+guard) eluting with 65% $CH_3CN/35\%$ of 0.1% $H_3PO_4$ in $H_2O$ at a flow rate of 24 mL/min. Fractions were collected at 1 minute intervals (detecting wavelength=220 nm). Fractions were combined as shown below and each of the pools was analyzed by analytical HPLC and then extracted with an equal volume of EtOAc. The organic layer was evaporated to dryness to afford dry material.

The analytical HPLC conditions involved a reverse-phase silica-based HPLC column (Dynamax C8, 60

The 738 component has a molecular weight of 738 by FAB-MS (obse ved [M-H]⁻ at m/z 737) and a molecular formula $C_{40}H_{50}O_{13}$ as determined by HR-EI measurement of the trimethylester derivative [calc. for $(C_{40}H_{50}O_{13}+(CH_2)_3$ —$H_2O)$ 762.3615, found 762.3612]. RRT=0.58.

Fractions 36–37: contains at least 2 compounds MW 726 and MW 740. The 726 component has a molecular weight of 726 by FAB-MS (observed [M-H]⁻ at m/z 725). The molecular formula $C_{39}H_{50}O_{13}$ was determined by HR-EI measurement of the dimethylester derivative [calc. for $(C_{39}H_{50}O_{13}+(CH_2)_2$ —$H_2O)$ 736.3459, found 736.3458]. It may be 4'-O-desacetyl-4'',5''-dihydro-zaragozic acid C monomethyl ester. RRT=0.74.

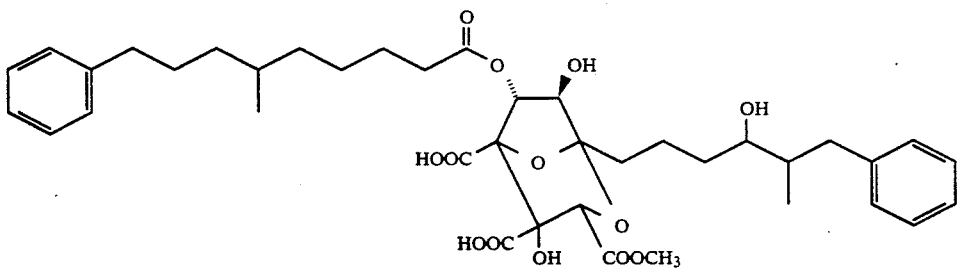

The second component has a molecular weight of 740 by FAB-MS (observed [M-H]− at m/z 739). The molecular formula $C_{39}H_{48}O_{14}$ was determined by HR-EI measurement of the trimethylester derivative [calc. for $(C_{39}H_{48}O_{14}+C_3H_6$ —$CH_3COOH)$ 722.3302, found 722.3304].

Fractions 38-39: This contains a compound of MW 752, by FAB-MS (observed [M-H]− at m/z 751). The molecular formula $C_{40}H_{48}O_{14}$ was determined by HR-EI measurement of the trimethylester derivative [calc. for $(C_{40}H_{48}O_{14}+C_3H_6$ —$CH_3COOH)$ 734.3302, found 734.3299]. RRT=0.81. It may be 8″,9‴-dehydrozaragozic acid C, of the structure:

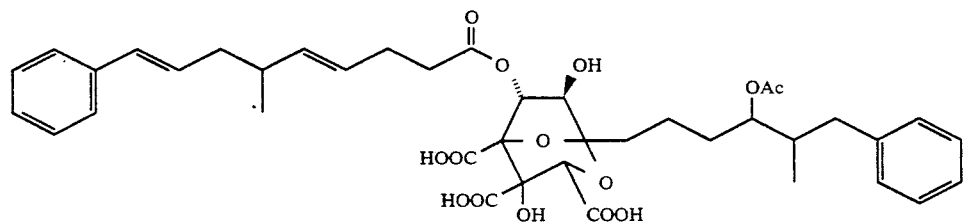

Cut 10-11
Contains zaragozic acid C: MW 754 (41.9 g) RRT=1.00.

Cut 12-14
Two thirds of Cut 12-14 was partitioned with an equal volume of EtOAc. The organic layer was evaporated to dryness. One half of the dry residue was dissolved in 3 mL of $CH_3CN$/1 mL of 0.1% $H_3PO_4$ in $H_2O$. This solution was injected on a preparative HPLC column (Dynamax C8 8 μm 41.4 mm ID×250 mm L+guard) eluting with 70% $CH_3CN$/30% of 0.1% $H_3PO_4$ in $H_2O$ at a flow rate of 24 mL/min. Fractions were collected at 1 min intervals (detecting wavelength=220 nm). Fractions were combined as shown below and each of the pools was analyzed by analytical HPLC and then extracted with an equal volume of EtOAc. The organic layer was evaporated to dryness to afford dry material.

The analytical HPLC conditions involved a reverse-phase silica-based HPLC column (Dynamax C8, 60 Angstroms, 8 μm particles, 4.6 mm ID×250 mm with guard column) eluting at room temperature at a flow rate of 1 ml/min with a mobile phase of 65% $CH_3CN$/35% of 0.1% $H_3PO_4$ in $H_2O$. The detection wavelength was 205 nm. Relative retention time to zaragozic acid C(RRT) is calculated for each compound as the ratio of the retention time of a given major peak divided by the retention time of zaragozic acid C. (11.5 min).

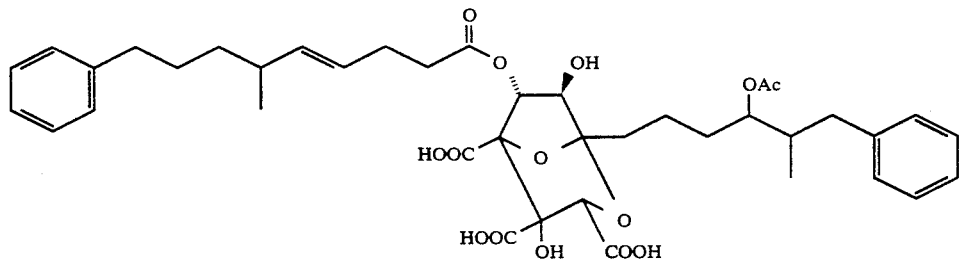

Fractions 30-31 (284.5 mg): contains zaragozic acid C MW 754

Fractions 35-36 (78.9 mg): contains a compound of MW 756 by FAB-MS (observed [M-H]− at m/z 755). The molecular formula $C_{40}H_{52}O_{14}$ was determined by HR-EI measurement of the trimethylester derivative [calc. for $(C_{40}H_{52}O_{14}+(CH_2)_3$—$CH_3COOH)$ 738.2615, found 738.3611]. RRT=1.10. It may be 4″,5″-dihydrozaragozic acid C:

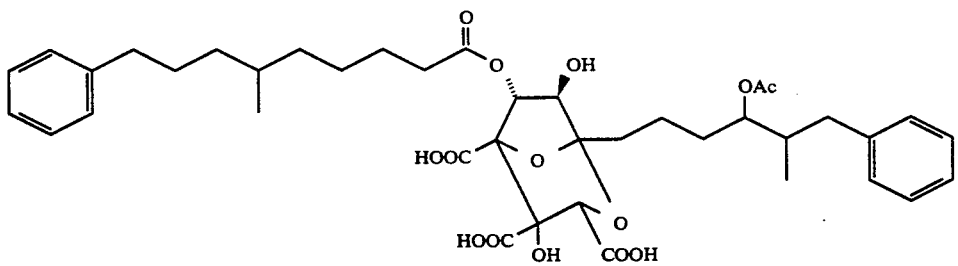

Fractions 39–40 (34.6 mg): contains 4'-desacetoxy zaragozic acid C MW 696

Cut 15–17

Contains 4'-desacetoxy zaragozic acid C (L-735,021); MW 696 (9.7 g). RRT=1.3.

Fractions 35–36 (19.4 mg): The major component in this fraction has a molecular weight of 698 by FAB-MS (observed [M-H]⁻ at m/z 697). The molecular formula $C_{38}H_{50}O_{12}$ was determined by HR-EI measurement of the trimethylester derivative [calc. for

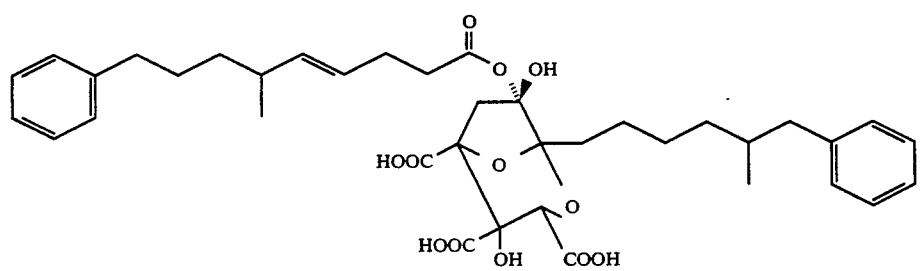

Cut 18–20

Half of cut 18–20 was partitioned with an equal volume of EtOAc. The organic layer was evaporated to dryness. One fifth of the dry residue was dissolved in 3 mL of $CH_3CN$/1 mL of 0.1% $H_3PO_4$ in $H_2O$. This solution was injected on a preparative HPLC column (Dynamax C8 8 μm 41.4 mm ID×250 mm L+guard) eluting with 75% $CH_3CN$/25% 0.1% $H_3PO_4$ in $H_2O$ at a flow rate of 24 mL/min. Fractions were collected at 1 min intervals (detecting wavelength=220 nm). Fractions were combined as shown below and each of the pools was analyzed by analytical HPLC and then extracted with an equal volume of EtOAc. The organic layer was evaporated to dryness to afford dry material.

The analytical HPLC conditions involved a reverse-phase silica-based HPLC column (Dynamax C8, 60 Angstroms, 8 μm particles, 4.6 mm ID×250 mm with guard column) eluting at room temperature at a flow rate of 1 ml/min with a mobile phase of 65% $CH_3CN$/35% of 0.1% $H_3PO_4$ in $H_2O$. The detection wavelength was 205 nm. Relative retention time to zaragozic acid C(RRT) is calculated for each compound as the ratio of the retention time of a given major peak divided by the retention time of zaragozic acid C. (11.5 min).

Fractions 31–32 (34.6 mg): contains 4'-desacetoxy zaragozic acid C MW 696. RRT=1.3.

$(C_{38}H_{50}O_{12}+(CH_2)_3)$ 740.3771, found 740.3770]. May contain 4'-desacetoxy dihydrozaragozic acid C MW 698. RRT=1.5.

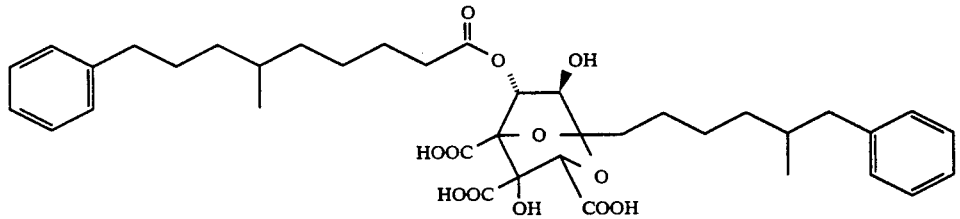

Fractions 46–47 (9.1 mg): contains a major component with the molecular weight of 696 by FAB-MS (observed [M-H]⁻ at m/z 695). The molecular formula $C_{38}H_{48}O_{12}$ was determined by HR-EI measurement of the trimethylester derivative [calc. for $(C_{38}H_{48}O_{12}+(CH_2)_3)$ 738.3615, found 738.3618]. RRT=2.0.

Fractions 52–54 (15.8 mg): contain two components MW 676 and 736. The 676 component, FAB-MS (observed [M-H]⁻ at m/z 675), forms a trimethylester observed at m/z 700 (676+$(CH_2)_3$—$H_2O$). The 736 component [FAB-MS (observed [M-H]⁻ at m/z 735)] has a molecular formula $C_{40}H_{48}O_{13}$ as determined by HR-EI measurement of the dimethylester derivative [calc. for $(C_{40}H_{48}O_{13}+C_2H_4$ —$CH_3COOH)$ 718.3353, found 718.3354]. RRT=2.5.

Fractions 61–62 (9.7 mg): contains a major component MW 678, by FAB-MS (observed [M-H]⁻ at m/z 677) which forms a trimethylester at m/z 720 (678+$(CH_2)_3$). RRT=2.7.

Fractions 65–66 (11.2 mg): contains a major component MW 750, by FAB-MS (observed [M-H]⁻ at m/z 749). RRT=2.8.

The isolated compounds of this Example are summarized in the following Table. It will be understood that the particulars of this Table are subject to minor revisions as additional tests become available subsequent to the filing of this application.

TABLE

| MW | Molecular Formula | Relative Retention Time (RRT) | Cut/Fractions* |
|---|---|---|---|
| 676 | n/a | 2.5 | 18-20/52-54 |
| 678 | n/a | 2.7 | 18-20/61-62 |
| 696 | $C_{38}H_{48}O_{12}$ | 1.3 | 15-17 |
| 696 | $C_{38}H_{48}O_{12}$ | 2.0 | 18-20/46-47 |
| 698 | $C_{37}H_{46}O_{13}$ | 0.38 | 5-6/31 |
| 698 | $C_{38}H_{50}O_{12}$ | 1.5 | 18-20/35-36 |
| 700 | $C_{37}H_{48}O_{13}$ | 0.46 | 5-6/36 |
| 710 | $C_{38}H_{46}O_{13}$ | 0.30 | 5-6/27-28 |
| 710 | $C_{38}H_{46}O_{13}$ | 0.41 | 5-6/33 |
| 712 | $C_{38}H_{48}O_{13}$ | 0.38 | 5-6/31 |
| 712 | $C_{38}H_{48}O_{13}$ | 0.49 | 7,5-6/38 |
| 714 | $C_{38}H_{50}O_{13}$ | 0.58 | 8-9/31-32 |
| 726 | $C_{39}H_{50}O_{13}$ | 0.74 | 8-9/36-37 |
| 728 | $C_{39}H_{52}O_{13}$ | 0.37 | 5-6/30 |
| 736 | $C_{40}H_{48}O_{13}$ | 2.5 | 18-20/52-54 |
| 738 | $C_{40}H_{50}O_{13}$ | 0.58 | 8-9/31-32 |
| 740 | $C_{39}H_{48}O_{14}$ | 0.74 | 8-9/36-37 |
| 750 | n/a | 2.8 | 18-20/65-66 |
| 752 | $C_{40}H_{48}O_{14}$ | 0.81 | 8-9/38-39 |
| 754 | $C_{40}H_{50}O_{14}$ | 1.00 | 10,11 |
| 756 | $C_{40}H_{52}O_{14}$ | 1.10 | 12-14/35-36 |
| 768 | n/a | 0.41 | 5-6/33 |
| 770 | n/a | 0.30 | 5-6/27-28 |

*Cut refers to combined fractions from the large scale HFLC/fractions refers to HPLC fractions from the fractionation of the cuts.

EXAMPLE 4

Preparation of an Ammonium Salt

A 0.1 mmol sample of the free acid of a compound of formula (I) is dissolved in 10 ml of ethyl acetate. The resulting solution is saturated with gaseous ammonia upon which the ammonium salt precipitates from solution.

EXAMPLE 5

Preparation of a Potassium Salt

A solution of 0.1 mmol of the free acid of a compound of formula (I) in 10 ml of methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion the sodium and lithium salts can be formed.

EXAMPLE 6

Preparation of a Calcium Salt

A solution of 0.1 mmol of the free acid of a compound of formula (I) in 20 ml of 6:4 methanol/water is treated with an aqueous solution of 0.1 mmol of calcium hydroxide. The solvents are evaporated to give the corresponding calcium salt.

EXAMPLE 7

Preparation of an Ethylenediamine Salt

A solution of 0.1 mmol of the free acid of a compound of formula (I) in 10 ml of methanol is treated with 0.1 mmol of ethylenediamine. Evaporation of the solvent affords the ethylenediamine salt. The procedure can also be applied to the preparation of the N,N''-dibenzylethylenediamine salt.

EXAMPLE 8

Preparation of a Tris(hydroxymethyl)aminomethane Salt

To a solution of 0.1 mmol of the free acid of a compound of formula (I) in 10 ml of methanol is added from 0.1 to 0.3 mmol of tris(hydroxymethyl) aminomethane dissolved in 10 ml of methanol. Evaporation of the solvent gives a corresponding salt form, the exact composition of which is determined by the molar ratio of amine added. Similarly prepared are the salts of L-ornithine, L-lysine, and N-methylgluacamine.

EXAMPLE 9

Preparation of an L-arginine Salt

A solution of 0.1 mmol of the free acid of a compound of formula (I) in 20 ml of 6:4 methanol/water is treated with an aqueous solution of 0.1 to 0.3 mmol of L-arginine. Evaporation of the solvent affords the title salt, the exact composition of which is determined by the molar ratio of amino acid to the free acid of formula (I) used.

Similarly prepared are the salts of L-ornithine, L-lysine and N-methylglucamine.

EXAMPLE 10

Preparation of A trimethyl ester

A solution of 2 mg of a free acid of compound of formula (I) in 0.5 ml of acetonitrile is treated at room temperature with 10 equivalents of DBU and 10 equivalents of MeI. After 2 hours the reaction is diluted with 10 ml of dichloromethane and washed successively with 10 ml of 0.1M phosphoric acid, 10 ml of water, 10 ml of saturated sodium bicarbonate and 10 ml of water. After drying over sodium sulfate, the organic layer is concentrated and the residue is chromatographed on silica gel using mixtures of hexane and ethyl acetate to give a trimethyl ester The method of Example 7 is also suitable for the preparation of other ester derivatives such as 1) ethyl and other lower alkyl esters and 2) benzyl and substituted benzyl esters.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and its equivalents.

What is claimed is:

1. A compound of the structural formula (I)

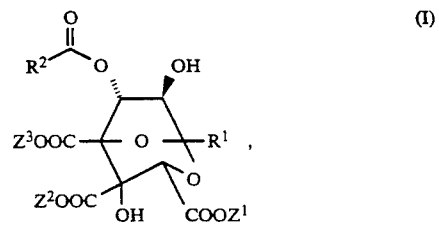

or pharmaceutically acceptable salt thereof, wherein

R¹ is selected from the group consisting of

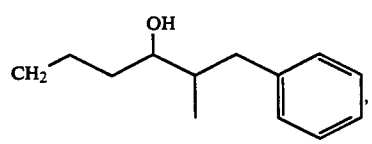

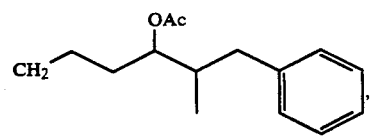

or

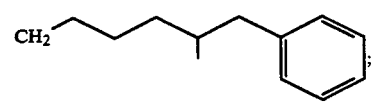

R² is selected from the group consisting of

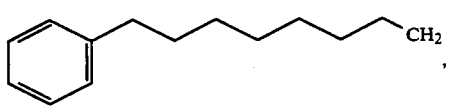

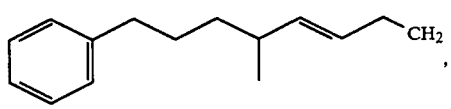

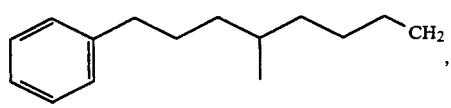

or

Z¹, Z² and Z³ are each independently selected from;
a) H;
b) $C_{1-5}$alkyl;
c) $C_{1-5}$alkyl substituted with a member of the group consisting of:
i) phenyl,
ii) phenyl substituted with methyl, methoxy, halogen (Cl, Br, I, F) or hydroxy;

with the proviso that when R² is

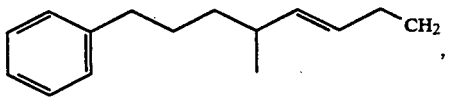

then R¹ is neither

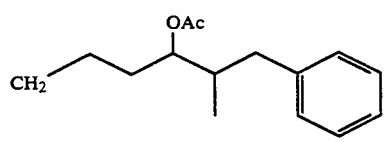

nor

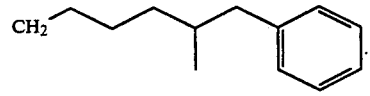

2. A compound according to claim 1, wherein Z¹, Z² and Z³ are each independently H or $CH_3$.

3. A compound according to claim 1, of the structure

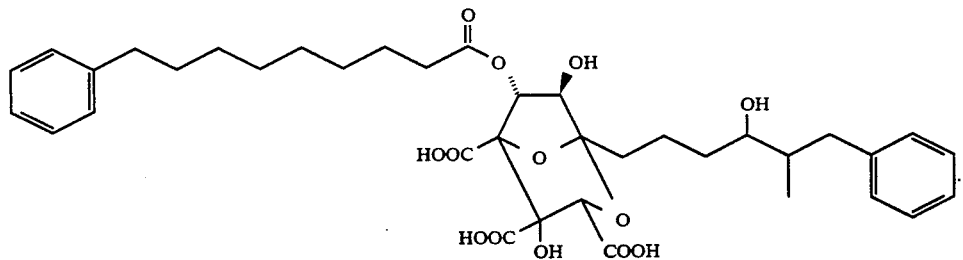

4. A compound according to claim 1, of the structure

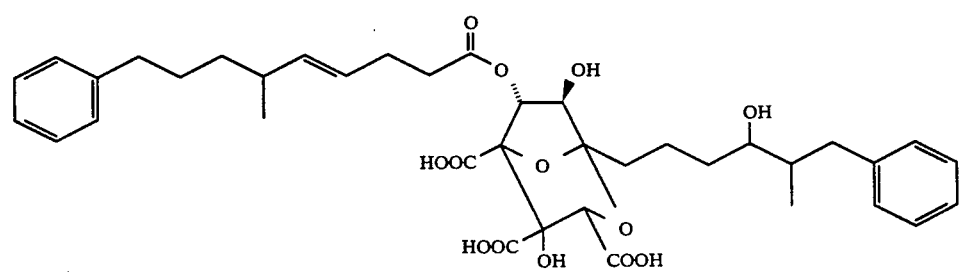

5. A compound according to claim 1, of the structure
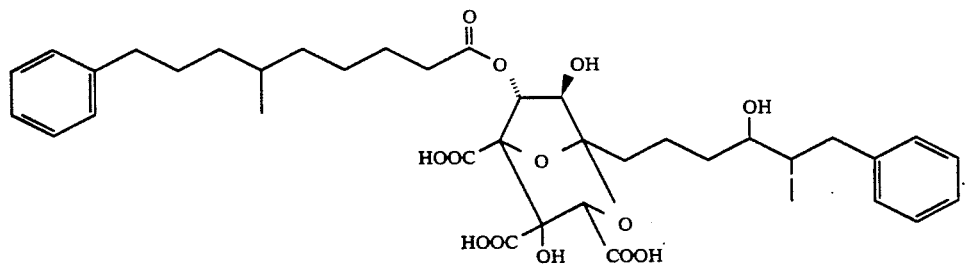
6. A compound according to claim 1, of the structure
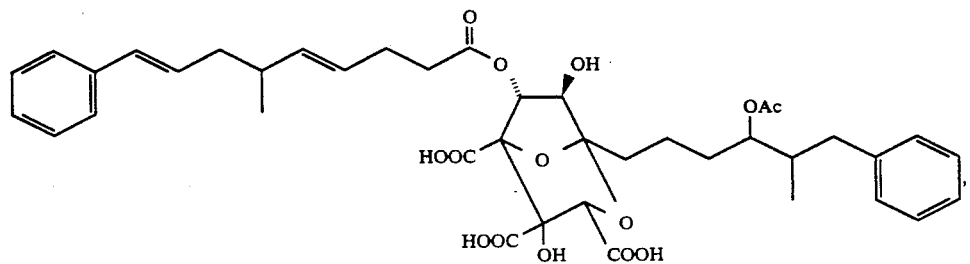
7. A compound according to claim 1, of the structure
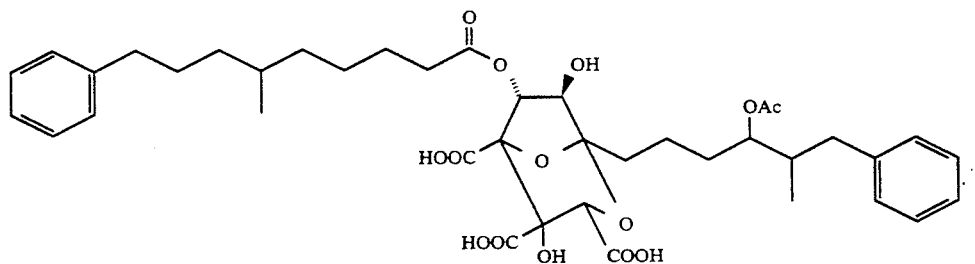
8. A compound according claim 1, of the structure
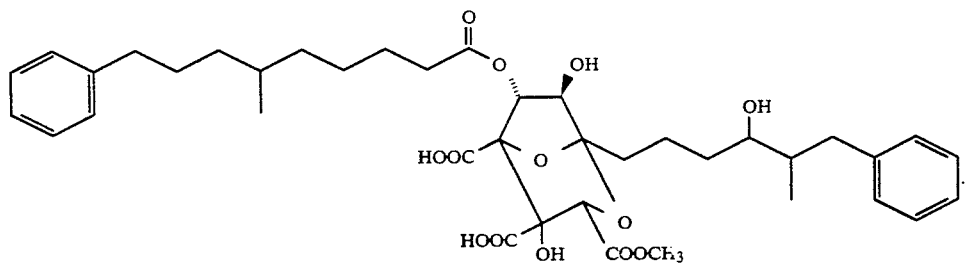
9. A compound according to claim 1, of the structure
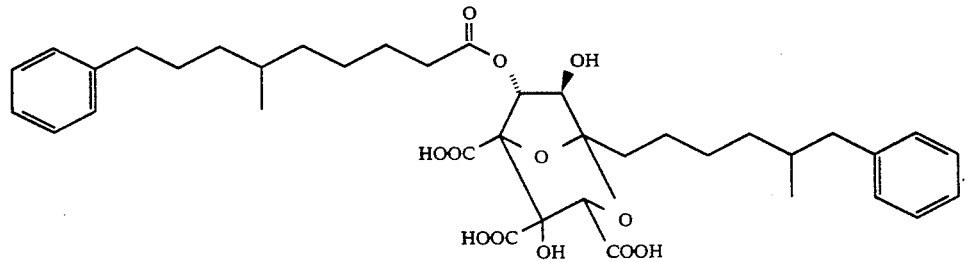
* * * * *